United States Patent [19]

Leonard

[11] Patent Number: 4,883,455

[45] Date of Patent: Nov. 28, 1989

[54] CARDIOPLEGIA ADMINISTRATION SET

[75] Inventor: Ronald J. Leonard, Saint Paul, Minn.

[73] Assignee: Minnesota Mining and Manufacturing Company, St. Paul, Minn.

[21] Appl. No.: 243,896

[22] Filed: Sep. 13, 1988

[51] Int. Cl.$^4$ ............................................ A61M 37/00
[52] U.S. Cl. ...................................... 604/4; 604/113; 128/DIG. 3; 422/46
[58] Field of Search .................. 604/4, 27, 29, 113, 604/122, 123; 128/DIG. 3, 400; 422/44, 46

[56] References Cited

U.S. PATENT DOCUMENTS

| | | | |
|---|---|---|---|
| 4,427,009 | 1/1984 | Wells | 128/400 |
| 4,515,589 | 5/1985 | Austin et al. | 604/122 |
| 4,568,330 | 2/1986 | Kujawski et al. | 604/53 |
| 4,650,471 | 3/1987 | Tamari | 604/153 |
| 4,705,508 | 11/1987 | Karnavas et al. | 604/113 |
| 4,767,289 | 8/1988 | Parrott et al. | 417/477 |

OTHER PUBLICATIONS

BCD Plus Blood Cardioplegia System, Shiley Incorporated 1986.
"Why Would any Company in its Right Mind Tamper with Success?", 1986 Shiley, Inc.
Buckberg-Shiley Blood Cardioplegia Solution Delivery Set, Shiley Incorporated 1984.
D720 High Efficiency Heat Exchanger for Blood Cardioplegia, Electromedics, Inc.
D720 Helios, Dideco S.p.A. and Electromedics, Inc.

Primary Examiner—Jerome L. Kruter
Attorney, Agent, or Firm—Donald M. Sell; Walter N. Kirn; Robert W. Hoke, II

[57] ABSTRACT

A cardioplegia administration set including a heat exchanger, a bubble trap, a three-end connector, a normally-closed, pressure-responsive valve and interconnecting tubing. A first tubing means having an inlet adapted to be connected to a source of cardioplegia solution and an outlet connected to an inlet of the three-end connector interconnects inlets and outlets of the heat exchanger and the bubble trap therebetween so that a solution passageway is established from the source of cardioplegia solution through the heat exchanger and the bubble trap to an end of the three-end connector adapted to connect to an injection catheter. A second tubing means has an inlet connected to a recirculation outlet of the three-end connector and an outlet adapted to be connected to the source of cardioplegia solution so that a solution passageway is established from the three-end connector through the normally-closed valve back to the source of cardioplegia solution when the valve is open. The second tubing means and the normally-closed, pressure-responsive valve together comprise a recirculation loop.

34 Claims, 3 Drawing Sheets

CARDIOPLEGIA ADMINISTRATION SET

REFERENCE TO COPENDING APPLICATION

Reference is made to a copending application Ser. No. 219,325 by Ronald J. Leonard, the same named inventor of the subject matter of the present application, entitled "COMBINATION FLUID PATH AND MOUNT FOR HEAT EXCHANGER", filed July 15, 1988 and assigned to the same assignee.

FIELD OF THE INVENTION

This invention relates to extracorporeal life support systems for cardiovascular surgery and particularly to cardioplegia administration sets for cooling, debubbling and delivering drugs for injection into the heart during such surgery to provide myocardial protection.

BACKGROUND ART

Cardiovascular surgery is practiced with many forms of myocardial protection. The need for myocardial protection during such surgery is caused by the medical practice of draining the venous blood from the heart into an extracorporeal oxygenator, oxygenating the blood, and returning the oxygenated blood to the heart downstream of the coronary arteries; that is, the heart muscle itself is denied the benefit of oxygenated blood during many of these surgeries. This of course risks ischemic damage to the heart muscle.

One common form of myocardial protection is the use of cardioplegia solution to cause temporary paralysis of the heart. This elective stopping of cardiac activity is known to be accomplished by the injection of chemicals, selective hypothermia, electrical stimuli or a combination of these techniques. A typical combination is the injection of a cold cardioplegia solution directly into the heart circulation. Known cold cardioplegia solutions include "clear" cardioplegia, "crystalloid" cardioplegia and "blood" cardioplegia.

In the case of each of these solutions, the solution at the time of the surgery is pumped from a source through an administration set, sometimes called a tube set, and injected into the patient's heart after being suitably cooled and debubbled. A typical pump for such applications is known as a roller pump. This is a form of positive displacement pump that will develop considerable head pressures and resultant patient delivery pressures that may be medically unacceptable and capable of damaging the tube set in the case, for example, of an obstruction downstream of the pump. Partially because of this capability, these administration sets are carefully moderated to control the delivery pressure to the heart, and sometimes are provided with weaker portions in the form of pop-off valves. These pumps are typically turned off when the attending medical personnel do not desire the delivery of the cooled and debubbled cardioplegia solution into the patient's heart. However, when the pump is turned off, much of the cardioplegia solution within the tube set is not being cooled. This allows rewarming of the solution to ambient conditions and partial loss of the therapeutic hypothermia.

SUMMARY OF THE INVENTION

The present invention provides a cardioplegia administration set having a recirculation loop so that the solution can be continually cooled and debubbled in the event the tube set is intentionally or unintentionally partially or totally obstructed adjacent the patient's heart. According to the invention, there is provided a cardioplegia administration set suitable for delivering cool cardioplegia solution to the heart on demand for injection into the heart to provide myocardial protection during cardiovascular surgery. The administration set comprises a heat exchanger, a bubble trap, a three-end connector, a normally-closed, pressure-responsive valve and interconnecting tubing. The heat exchanger and the bubble trap have inlets and outlets. The three-end connector has one end adapted to connect to a cardioplegia solution injection catheter, one end comprising an inlet and one end comprising a recirculation outlet. A first tubing means having an inlet adapted to be connected to a source of cardioplegia solution and an outlet connected to the inlet of the three-end connector interconnects the inlets and the outlets of the heat exchanger and the bubble trap therebetween so that a solution passageway is established from the source of cardioplegia solution through the heat exchanger and through the bubble trap to the end of the three-end connector adapted to connect to the injection catheter. A second tubing means has an inlet connected to the recirculation outlet of the three-end connector and an outlet adapted to be connected to the source of cardioplegia solution so that a solution passageway is established from the three-end connector through the normally-closed valve back to the source of cardioplegia solution when the valve is open. The second tubing means and the normally-closed, pressure-responsive valve together comprise a recirculation loop.

In a preferred embodiment, the valve comprises a normally-closed-in-cross-section and openable-in-response-to-positive-fluid-pressure inner tube, a housing receiving the inner tube, an inlet portion connecting the housing to the inlet of the inner tube and an outlet portion connecting the housing to the outlet of the inner tube so that the cardioplegia solution can be delivered to the patient at a predetermined pressure in the range of about 50-150 mmHg. Also in a preferred embodiment, the heat exchanger and the bubble trap are combined and comprise a combination fluid path and mount as more fully described hereinafter.

DESCRIPTION OF THE DRAWING

Other advantages of the invention will become apparent from the following drawing wherein like numerals refer to like parts.

DETAILED DESCRIPTION

Figure 1:
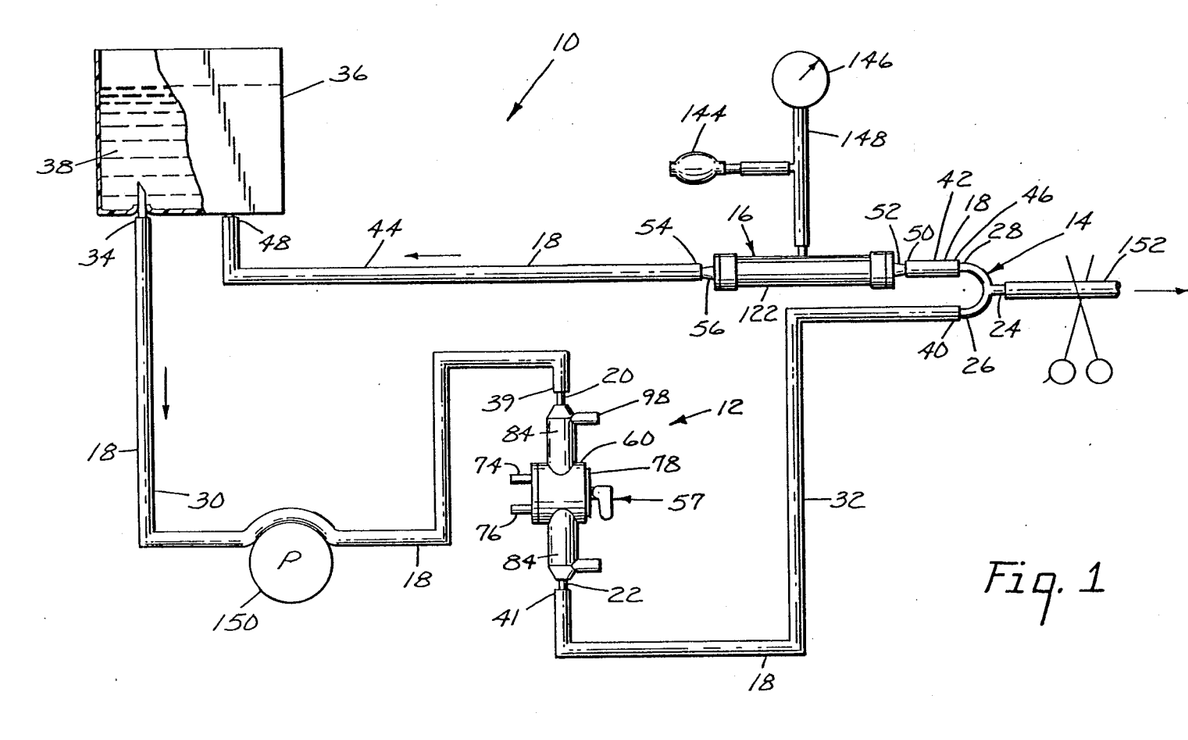
FIG. 1 is a schematic view of a preferred embodiment of the administration set of the present invention, including a preferred normally-closed, pressure-responsive valve and a preferred combination bubble trap and heat exchanger, suitable for continually cooling and debubbling cardioplegia solution for delivery to a patient's heart on demand for injection into the heart at a predetermined pressure in the range of about 50-150 mmHg.

Referring to the figures of the drawing, there is shown in FIG. 1 a schematic view of a preferred embodiment of the administration set 10 of the present invention suitable for cooling, debubbling and delivering cardioplegia solution to on demand for injection into the heart at a predetermined pressure in the range of about 50–150 mmHg. The set 10 is generally comprised of a combination bubble trap and heat exchanger 12, a hollow-bodied, three-end connector 14, a normally-closed, pressure-responsive valve 16 and interconnecting medical-grade tubing 18.

The combination bubble trap and heat exchanger 12 has an inlet 20 and an outlet 22. The three-end connector has one end 24 adapted to connect, via a tubing 152, to a cardioplegia solution injection catheter (not shown), one end comprising an inlet 26 and one end comprising a recirculation outlet 28. A first tubing means, including tubing 30 and 32, has an inlet 34 connected to a source 36 of cardioplegia solution 38 and an outlet 40 connected to the inlet 26 of the three-end connector 14 and interconnects the inlet 20 and the outlet 22 of the bubble trap/heat exchanger 12 therebetween so that a solution passageway is established from the source 36 of cardioplegia solution 38 through the bubble trap/heat exchanger 12 to the end 24 of the three-end connector 14 adapted to connect to the injection catheter. More particularly, the inlet 34 of the tubing 30 is connected to the source 36 of the cardioplegia solution 38 via any suitable means such as barbed, piercing-needle as shown, and an outlet 39 of the tubing 30 is connected to the inlet 20 of the bubble trap/heat exchanger 12; an inlet 41 of the tubing 32 is connected to the outlet 22 of the bubble trap-heat exchanger 12, and the outlet 40 of the tubing 32 is connected to the inlet 26 of the three-end connector 14. The three-end connector is preferably comprised of a transparent, rigid, medical-grade, acrylic material.

The preferred bubble trap/heat exchanger 12 is shown and will be described as of a single, combined structure. However, it is known to utilize separate bubble traps and heat exchangers having separate inlets and outlets, and such separate devices can be utilized in the administration set 10 of the present invention. In such case, the cardioplegia solution would normally preferably flow through the bubble trap before flowing through the heat exchanger, but these devices can be reversed.

A second tubing means including tubing 42 and 44 has an inlet 46 connected to the recirculation outlet 28 of the three-end connector 14 and an outlet 48 adapted to be connected to the source 36 of cardioplegia solution 38 so that a solution passageway is established from the three-end connector 14 through the normally-closed valve 16 back to the source 36 of cardioplegia solution 38 when valve 16 is open. More particularly, the inlet 46 of the tubing 42 is connected to the recirculation outlet 28 of the three-end connector 14, and an outlet 50 of the tubing 42 is connected to an inlet 52 of the valve 16; an inlet 54 of the tubing 44 is connected to an outlet 56 of the valve 16, and the outlet 48 of the tubing 44 is adapted to be conventionally connected to the source 36 of the solution 38. Preferably, all tubing connections between the inlet 34 and the outlet 48 are of a permanent and sealing nature and are the result of conventional cementing or radio-frequency sealing techniques.

Figure 2:
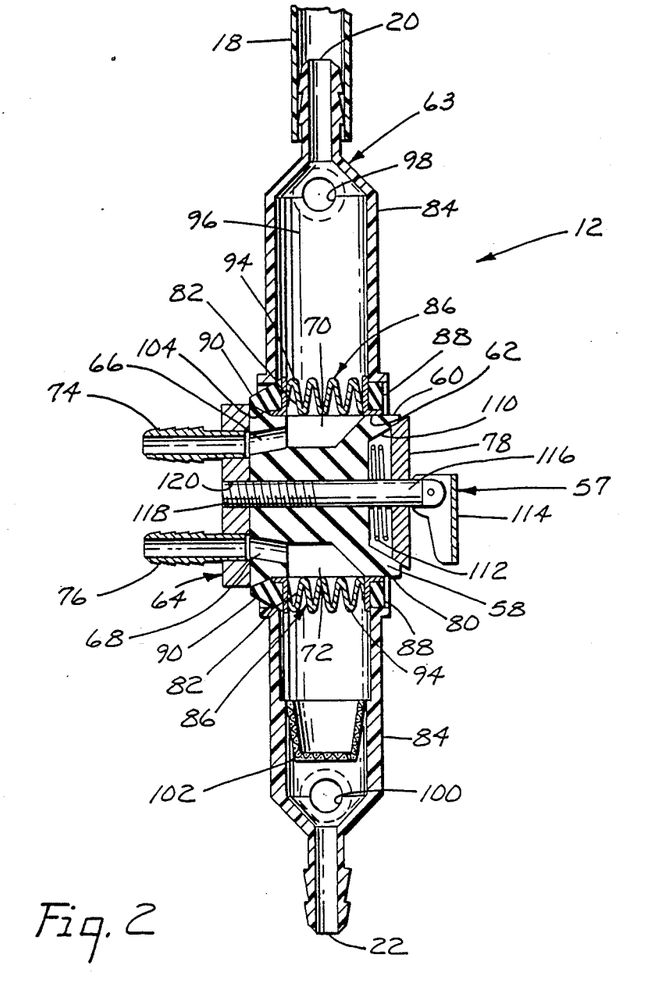
FIG. 2 is a transverse cross-sectional view of the preferred bubble trap and heat exchanger of FIG. 1.

As shown in FIG. 2, the bubble trap/heat exchanger 12 includes a combination mount and heat exchanging-fluid path 57 for mounting the bubble trap/heat exchanger 12 and supplying a suitable heat-exchanging fluid, such as water, to the heat exchanger 63. The mount/fluid path 57 generally comprises a generally cylindrical body 58 of generally flexible-resilient material having a periphery 60 adapted to be received in a fluid-path portion or passageway 62 of the heat exchanger 63, in which a heat-exchanging fluid circulates. Means, for example in the form of a bracket 64, is provided on the inner or rear end (the left end in FIG. 2) of the body 58 for mounting or clamping the body 58 on a support stand, not shown. As shown in FIG. 2, the body 58 has heat-exchanging fluid inlet and outlet passages 66 and 68 opening at 70 and 72, respectively, through the periphery 60 of the body 58 for circulating heat-exchanging fluid to the heat exchanger 63. Hose fittings 74 and 76, communicating with the inlet and outlet passageways 66 and 68, respectively, are provided on the bracket 64. Fixing-sealing means is provided for removably fixing the heat-exchanger 63 to the body 58 and sealing between the body 58 and the heat exchanger 63. The fixing-sealing means includes tapered means, for example frustoconical member 78, for expanding a portion 80 of the periphery of the body 58 radially outwardly against an inner surface 82 of the heat exchanger 63 to form a seal therebetween and to hold the heat exchanger 63 on the body 58. Alternatively, the fixing-sealing means may include suitable non-tapered means, such as a cylindrical or other shaped member (not shown) for expanding the portion 80 of the body 58 laterally outwardly against the inner surface 82 of the heat exchanger 63.

The heat exchanger 63 has the generally cylindrical passageway 62 in which the heat-exchanging fluid may be circulated and which is adapted for closely receiving the body 58 to mount the heat exchanger 63 on the body 58 such that the heat exchanging fluid is supplied to the heat exchanger 63 via the inlet passage 66 and removed via the outlet passageway 68. The heat exchanger 63 includes a generally transparent outer case 84 of synthetic resin material, for example acrylic resin or polycarbonate, and an undulated, annular barrier 86 for separating the cardioplegia solution 38 from the heat-exchanging fluid while permitting heat transfer through the barrier 86. The case 84 and the barrier 86 are sealingly innerconnected by conventional annular seals 88 and 90, for example of urethane or silicone sealant, adjacent opposite end portions of the barrier 86. The end portions of the barrier 86 have generally L-shaped cross-sections in the direction longitudinally of the barrier 86 forming flat and cylindrical surfaces adapted for sealing engagement with the seals 88 and 90. The barrier 86 is preferably formed of material having a high thermal conductivity, such as stainless steel, and has the inner undulated surface 82 defining the body-receiving and fluid-circulating passageway 62 as generally cylindrical and complimentary to the body 58, and has an outer undulated surface 94 in the case 84 along which the cardioplegia solution 38 flows through the case 84 between the inlet 20 at an "upper" end of the case 84 and the outlet 22 at the opposite or "lower" end of the case 84. The inner and outer undulated surfaces 82 and 94 of the barrier 86 form a plurality of generally annular channels running circumferentially around the barrier 86. It will be observed that if the body 58 is sufficiently closely received within the passageway 62, formed by the inner surface 82 of the barrier 86, the heat-exchanging fluid will be forced into the annular channels formed by the undulations of the inner surface 82 to facilitate heat transfer between the fluid and the cardioplegia solution 38 across the barrier 86.

The case 84 includes a bubble trap 96 formed by the relatively large internal space adjacent the upper or inlet 20 end of the cardioplegia solution path for separating and trapping gas from the solution 38 so that the gas may be vented through a gas relief passageway 98 and manually actuatable valve, not shown, when sufficient gas has collected in the bubble trap 96. A thermowell 100 is provided adjacent the lower end or outlet 22 of the case 84 for receiving a temperature sensor, not shown, so that the temperature of the cardioplegia solution 38 flowing from the heat exchanger 63 may be measured. A suitable filter screen 102 may be positioned within the case 84 between the barrier 86 and the outlet 22 for filtering the cardioplegia solution 38 flowing through the heat exchanger 63. The heat exchanger 63 is adapted to be turned on the cylindrical body 58 between a priming position wherein the bubble trap 96 is positioned below the body 58 and cardioplegia solution 38 flows upwardly from the inlet 20 to fill the heat exchanger 63 and a ready position as shown in FIG. 2 wherein the bubble trap 96 is positioned above the body 58 and solution 38 flows downwardly from the inlet 20 through the heat exchanger 63 and gas bubbles migrate upwardly, against the flow, into the bubble trap 96.

The cylindrical body 58 is formed of generally elastomeric material such as silicone rubber or urethane having a Shore A durometer of between about 60 and 90. The body 58 is preferably flared radially outwardly at 104 adjacent the bracket 64 to provide a seal between the flared portion 104 of the body 58 and the corresponding end of the barrier 86. The heat-exchanging fluid inlet and outlet passages 66 and 68 have openings 70 and 72, respectively, formed in the circumferential surface of the body 58 along opposite sides of the body 58 for supplying heat exchanging fluid to the heat exchanger 63 and removing heat-exchanging fluid from the heat exchanger 63. The openings 70 and 72 are preferably elongate in the direction longitudinally or axially of the body 58 so that the heat-exchanging fluid flows along substantially the entire inner surface 82 of the barrier 86 between the inlet and outlet openings 70 and 72.

The body 58 has a generally cylindrical or frustoconical recess 110 extending substantially coaxially into the body 58 from the outer end of the body 58, that is, the end which is opposite the bracket 64, toward the bracket 64. The frustoconical member 78 and recess 110 are sized and configured such that when the member 78 is inserted in the recess 110, the portion 80 of the body 58 adjacent the recess 110 is expanded radially outwardly by the member 78 to form a seal between portion 80 and the end of the barrier 86 adjacent the outer end of the body 58. Spring means such as coil spring 112 is provided in the recess 110 between the member 78 and the base of the recess 110 for biasing the member 78 longitudinally or axially outwardly, that is rightwardly in FIG. 2, from the recess 110 of the body 58 to a non-sealing position wherein portion 80 is not expanded radially outwardly so that the heat exchanger 63 can be placed on the body 58 with the body 58 received in the heat-exchanging fluid passageway 62 and the heat exchanger 63 can be removed from the body 58. The member 78 is movable against the spring bias longitudinally or axially inwardly, leftwardly in FIG. 2, into the recess 110 to a sealing position wherein the portion 80 of the body 58 against the recess 110 is expanded radially outwardly by the member 78 to hold and seal the heat exchanger 63.

Preferably, a releasable locking means is provided for pulling the member 78 toward the bracket 64 into the recess 110 and holding it in the recess 110 in its sealing position. For example, the releasable locking means may include an overcenter locking mechanism 114 for securely holding the member 78 into the recess 110, and an adjusting bolt 116, connected to the locking mechanism 114 and extending longitudinally through the body 58 between the locking mechanism 114 and the bracket 64. A cam portion of the overcenter locking mechanism 114 moves the member 78 from its non-sealing position to its sealing position as the handle of the mechanism is pivoted inwardly relative to the adjusting bolt 116. An inner threaded end 118 of the bolt 116 is received in a corresponding threaded bore 120 of the bracket 64 so that the distance between the overcenter mechanism 114 and the bracket 64 can be varied by turning the bolt 116 to adjust the sealing and non-sealing positions of the member 78.

Other embodiments of the bubble trap/heat exchanger 12 can be utilized in the administration set 10 of the present invention. Such other bubble traps and heat exchangers are described in copending application Ser. No. 219,325 by Ronald J. Leonard, the same named inventor of the subject matter of the present application, entitled "COMBINATION FLUID PATH AND MOUNT FOR HEAT EXCHANGER", filed July 15, 1988, assigned to the same assignee and incorporated herein by reference.

Figure 3:
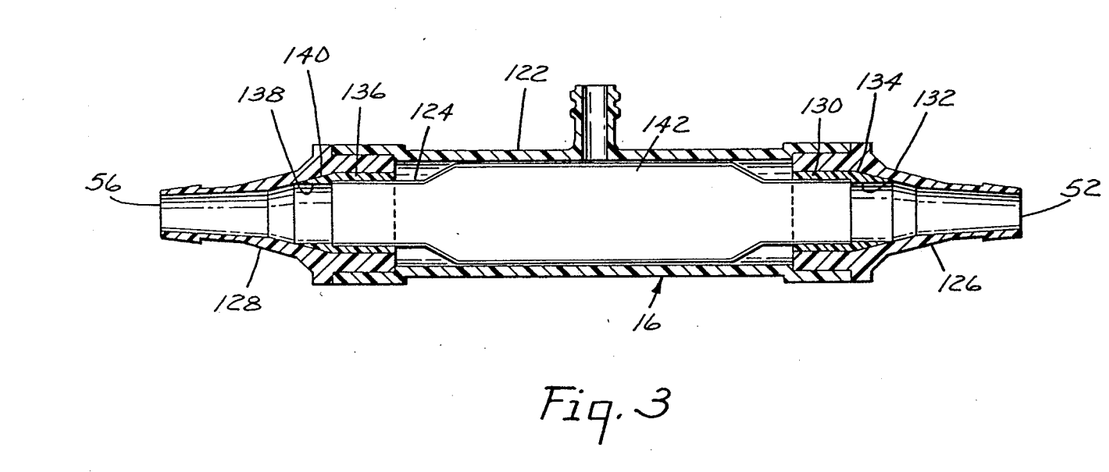
FIG. 3 is a transverse cross-sectional view of the preferred normally-closed, pressure-responsive valve of FIG. 1.

As shown in FIG. 3, the normally-closed, pressure-responsive valve 16 generally comprises a housing 122 receiving an inner tube 124, an inlet portion 126 connecting the housing 122 to the inner tube 124 adjacent the inlet 52 of the valve 16 and an outlet portion 128 connecting the housing 122 to the inner tube 124 adjacent the outlet 56 of the valve 16. In the preferred embodiment shown in FIG. 3, a first annular member 130 has a first and preferably inner wall 132 sealingly affixed to the inner tube 124 and a second preferably outer wall 134 sealing affixed to the inlet portion 126 by conventional cementing or radio-frequency sealing techniques. Similarly, a second annular member 136 has a first and preferably inner wall 138 sealingly affixed to the inner tube 124 and a second preferably outer wall 140 sealingly affixed to the outlet portion 128 by conventional cementing or radio-frequency sealing techniques.

The housing 122, inlet portion 126, outlet portion 128, first annular member 130 and second annular member 136 are preferably comprised of a transparent, rigid, medical-grade, acrylic material, and the inner tube 124 is preferably comprised of a flexible, resilient, vinyl, urethane or silicone material. Most preferably, the inner tube comprises a vinyl tube with wall thickness in the range of about 0.015–0.020 inches. Such a material is Natvar-660 available from Natvar Company, Clayton, N.C., U.S.A. and has a flattened portion 142 formed by radio frequency sealing opposite edges of the portion 142.

During actual assembly of the valve 16, the distance between the first and second annular members 130 and 136 is controlled relative to the length of the flattened portion 142 of the inner tube 124 so that this portion 142 is tensioned in a normally closed in cross section state. This tension, in turn, fixes the opening and closing of this portion 142 in response to fluid pressure. Preferably, this portion opens and closes at a hydrostatic pressure head at the inlet 52 of the valve 16 in the range of about 50–150 mmHg above ambient atmospheric pressure. The exact opening and closing pressure is most preferably controlled by means for achieving and maintaining a pressure outside the inner tube 124 in the range of about 50–150 mmHg and most preferably at about 90 mmHg above ambient atmospheric pressure.

The preferred means for achieving this pressure is shown in FIGS. 1 and 3 to comprise a pressure infusor 144, a pressure gauge 146, interconnecting tubing 148 and an inlet 150 to the otherwise sealed interluminal space between the inner tube 124 and the housing 122. Suitable infusor 144, gauge 146 and tubing 148 can comprise a conventional sphygmomanometer, minus the patient cuff, available from W. A. BAUM CO. INC., Copiague, N.Y., U.S.A.

The use of the administration set 10 of the present invention will next be described in relation to FIG. 1. Before activating a solution pump 150, the tubing 152 between the end 124 of the connector 14 and the injection catheter, not shown, is typically clamped off to prevent solution flow to the patient. Next the pump 150 is activated. A suitable pump is available from 3M Sarns Inc, Ann Arbor, Mich., U.S.A. This causes cardioplegia solution 38 to flow from the source 36, which can be any suitable container such as a conventional solution bag, and to the combination bubble trap and heat exchanger 12 where the solution 38 is suitably debubbled and cooled. Out of the trap and exchanger 12, the solution 38 is pumped through the connector 14, through the valve 16 and back to the source 36. This results in a constantly debubbled and cooled flow of cardioplegia solution 38 through the connector 14.

Before unclamping tubing 152, the delivery pressure of the cardioplegia solution 38 is adjusted by the pressurization of the interluminal space between the inner tube 124 and the housing 122 with the pressure infusor 144. The selected pressure is indicated on the gauge 146. When this pressure is reached, the flattened portion 142 of the inner tube 124 opens to allow recirculation of the solution 38. This recirculation, in turn, allows the solution 38 to be maintained constantly debubbled and cooled for delivery to the patient when the tube 152 is unclamped.

If at any time the tube 152 becomes obstructed, for example by intentional reclamping or unintentional blockage, the patient and the administration set 10 are protected from excessive pressures by the opening of the normally-closed, pressure-responsive valve 16. At the same time, the hypothermic valve of the cardioplegia solution 38 is not lost since the solution 38 is constantly being administered to the patient or returned to the source 36 from which it is recooled before delivery to the patient.

From the foregoing it will be apparent that all of the objectives of this invention have been achieved by the administration set shown and described. It will also be apparent that various modifications and changes may be made by those skilled in the art without departing from the spirit of the invention as expressed in the accompanying claims. Because these modifications and changes may be made by one skilled in the art and without departing from the spirit of the invention, all matters shown and described are to be interpreted as illustrative and not in a limiting sense.

What s claimed is:

1. A cardioplegia administration set suitable for continually cooling and debubbling cardioplegia solution for delivery to a patient's heart on demand at a predetermined pressure for injection into the heart, said administration set comprising:
   A. a heat exchanger having an inlet and an outlet;
   B. a bubble trap having an inlet and an outlet;
   C. a three-end connector having one end adapted to connect to a cardioplegia solution injection catheter, one end comprising an inlet and one end comprising a recirculation outlet;
   D. first tubing means having an inlet adapted to be connected to a source of cardioplegia solution and an outlet connected to the inlet of the three-end connector, said tubing means interconnecting the inlets and the outlets of the heat exchanger and the bubble trap therebetween so that a solution passageway is established from the source of cardioplegia solution through the heat exchanger and through the bubble trap to the end of the three-end connector adapted to connect to the injection catheter; and
   E. a recirculation loop comprising:
      1. a normally-closed, pressure-responsive valve having an inlet and an outlet; and
      2. second tubing means having an inlet connected to the recirculation outlet of the three-end connector and an outlet adapted to be connected to the source of cardioplegia solution so that a solution passageway is established from the three-end connector through the normally-closed valve back to the source of cardioplegia solution when the valve is open.

2. The administration set according to claim 1 wherein said normally-closed, pressure-responsive valve comprises:
   A. a normally-closed-in-cross-section and openable-in-response-to-positive-fluid-pressure inner tube having an inlet and an outlet in fluid communication with the solution passageway between the three-end connector and the source of cardioplegia solution;
   B. a housing receiving said inner tube;
   C. an inlet portion connecting the housing to the inner tube adjacent the inlet of the inner tube; and
   D. an outlet portion connecting the housing to the inner tube adjacent the outlet of the inner tube.

3. The administration set according to claim 2 wherein said normally-closed, pressure-responsive valve further comprises:
   A. a first annular member having a first wall portion affixed to the inner tube and a second wall portion affixed to the inlet portion of the valve; and
   B. a second annular member having a first wall portion affixed to the inner tube and a second wall portion affixed to the outlet portion of the valve.

4. The administration set according to claim 3 further comprising means for achieving and maintaining an above-ambient pressure outside of the inner tube so that this pressure can be utilized for effecting the opening and closing of the inner tube.

5. The administration set according to claim 4 wherein said pressure is in the range of about 50–150 mmHg.

6. The administration set according to claim 1 further comprising a combination fluid path and mount of the type used to cool cardioplegia solution by transferring heat between the solution and a heat-exchanging fluid, the heat exchanger having an inner surface defining a passageway in which the heat-exchanging fluid flows, the combination comprising a body of generally flexible-resilient material having a periphery adapted to be received in the passageway of the heat exchanger, and means for mounting the body of a support, the body having heat-exchanging fluid inlet and outlet passageways for circulating heat-exchanging fluid to the passageway of the heat exchanger, fixing-sealing means for removably fixing the heat exchanger to the body and sealing between the body and the inner surface of the heat exchanger including means for expanding a portion of the periphery of the body against the inner surface of the heat exchanger to form a seal therebetween and to hold the heat exchanger on the body.

7. The administration set according to claim 6 wherein the body is generally cylindrical, the means for expanding a portion of the body including tapered means for expanding the portion of the body radially outwardly, the body having a recess at one end thereof for receiving the tapered means such that a portion of the body adjacent the recess is expanded radially outwardly by the tapered means.

8. The administration set according to claim 7 wherein the means for mounting the body on a support includes a bracket attached to the end of the body opposite the recess and clamp means on the bracket for clamping a support stand to mount the body thereon, the fixing-sealing means including releasable locking means for pulling the tapered means toward the bracket into the recess of the body and holding it in the recess, the releasable locking means including an overcenter locking mechanism for securely holding the tapered means in the recess, and an adjusting bolt connected to the locking mechanism and the bracket and extending longitudinally through the body between the locking mechanism and bracket, the heat-exchanging fluid inlet and outlet passageways having openings formed in the circumferential surface of the body along opposite sides of the body for supplying the heat-exchanging fluid to the heat exchanger and removing the fluid from the heat exchanger, the openings being elongate in the direction longitudinally or axially of the body.

9. The administration set according to claim 7 wherein the means for expanding a portion of the body includes spring means for biasing the tapered means longitudinally or axially outwardly from the recess of the body to a non-sealing position wherein the heat exchanger can be placed on the body with the body received in the heat exchanger and the heat exchanger can be removed from the body, the tapered means being movable against the spring bias longitudinally or axially inwardly into the recess to a sealing position wherein the portion of the body adjacent the recess is expanded radially outwardly by the tapered means to hold and seal the heat exchanger.

10. The administration set according to claim 9 wherein the tapered means includes a frustoconical member adapted to be received in the recess of the body such that the portion of the body adjacent the recess is expanded radially outwardly by the frustoconical member.

11. The administration set according to claim 10 wherein the fixing-sealing means includes releasable locking means for pulling the frustoconical member into the recess of the body and holding it in sealing position, the releasable locking means including an overcenter locking mechanism for securely holding the frustoconical member in sealing position.

12. The administration set according to claim 9 wherein the body is formed of generally elastomeric material having a Shore A durometer of between 60 and 90.

13. The administration set according to claim 9 wherein the means for mounting the body on a support includes a bracket attached to the end of the body opposite the recess and clamp means on the bracket for clamping a support stand to mount the body thereon.

14. The administration set according to the claim 13 wherein the generally cylindrical body is flared radially outwardly adjacent the bracket.

15. The administration set according to claim 13 wherein the heat-exchanging fluid inlet and outlet passageways have openings formed in the circumferential surface of the body along opposite sides of the body for supplying the heat-exchanging fluid to the heat exchanger and removing the fluid from the heat exchanger, the openings being elongate in the direction longitudinally or axially of the body.

16. The administration set according to claim 6 wherein the body is generally cylindrical, the heat exchanger including an undulated, annular barrier for separating the cardioplegia solution from the heat-exchanging fluid while permitting heat transfer through the barrier, the barrier having an inner undulated surface constituting the inner surface and defining the body-receiving passageway as generally cylindrical, and an outer undulated surface along which the solution flows.

17. The administration set according to claim 16 wherein the heat exchanger further includes a case sealingly connected to the barrier and forming a cardioplegia solution path along the barrier through the case, the case forming the bubble trap at one end of the blood/solution path for separating and trapping gas from the blood or solution, the case being adapted to be turned on the cylindrical body between a priming position wherein the bubble trap is positioned below the body and a ready position wherein the bubble trap is positioned above the body.

18. A cardioplegia administration set suitable for continually cooling and debubbling cardioplegia solution for delivery to a patient's heart on demand at a predetermined pressure for injection into the heart, said administration set comprising:

A. a heat exchanger having an inlet and an outlet;
B first fluid passageway means having an inlet adapted to connect to a source of cardioplegia solution and an outlet connected to the inlet of the heat exchanger so that the solution can flow from the source into the heat exchanger;
C. a bubble trap having an inlet and an outlet;
D. second fluid passageway means having an inlet connected to the outlet of the heat exchanger and an outlet connected to the inlet of the bubble trap so that the solution can flow from the heat exchanger into the bubble trap;
E. a three-end connector having one end adapted to connect to a cardioplegia solution injection catheter, one end comprising an inlet and one end comprising a recirculation outlet;
F. third fluid passageway means having an inlet connected to the outlet of the bubble trap and an outlet connected to the inlet of the three-end connector so that the solution can flow from the bubble trap into the three-end connector;
G. a normally-closed, pressure-responsive valve having an inlet and an outlet;

H. fourth fluid passageway means having an inlet connected to the recirculation outlet of the three-end connector and an outlet connected to the inlet of the valve so that the solution can flow from the connector into the valve; and I. fifth fluid passageway means having an inlet connected to the outlet of the valve and an outlet adapted to be connected to the source of cardioplegia solution so that the solution can flow from the valve back into the source when the valve is open, whereby the solution can be recirculated and thereby continually cooled even when the catheter is not injecting the solution into the patient's heart.

19. The administration set according to claim 18 wherein said normally-closed, pressure-responsive valve comprises:

A. a normally-closed-in-cross-section and openable-in-response-to-positive-fluid-pressure inner tube having an inlet and an outlet in fluid communication with the solution passageway between the three-end connector and the source of cardioplegia solution;

B. a housing receiving said inner tube;

C. an inlet portion connecting the housing to the inner tube adjacent the inlet of the inner tube; and D. an outlet portion connecting the housing to the inner tube adjacent the outlet of the inner tube.

20. The administration set according to claim 19 wherein said normally-closed, pressure-responsive valve further comprises:

A. a first annular member having a first wall portion affixed to the inner tube and a second wall portion affixed to the inlet portion of the valve; and B. a second annular member having a first wall portion affixed to the inner tube and a second wall portion affixed to the outlet portion of the valve.

21. The administration set according to claim 20 further comprising means for achieving and maintaining an above-ambient pressure outside of the inner tube so that this pressure can be utilized for effecting the opening and closing of the inner tube.

22. The administration set according to claim 21 wherein said pressure is in the range of about 50–150 mmHg.

23. The administration set according to claim 22 further comprising a combination fluid path and mount of the type used to cool cardioplegia solution by transferring heat between the solution and a heat-exchanging fluid, the heat exchanger having an inner surface defining a passageway in which the heat-exchanging fluid flows, the combination comprising a body of generally flexible-resilient material having a periphery adapted to be received in the passageway of the heat exchanger, and means for mounting the body on a support, the body having heat-exchanging fluid inlet and outlet passageways for circulating heat-exchanging fluid to the passageway of the heat exchanger, fixing-sealing means for removably fixing the heat exchanger to the body and sealing between the body and the inner surface of the heat exchanger including means for expanding a portion of the periphery of the body against the inner surface of the heat exchanger to form a seal therebetween and to hold the heat exchanger on the body.

24. The administration set according to claim 23 wherein the body is generally cylindrical, the means for expanding a portion of the body including tapered means for expanding the portion of the body radially outwardly, the body having a recess at one end thereof for receiving the tapered means such that a portion of the body adjacent the recess is expanded radially outwardly by the tapered means.

25. The administration set according to claim 24 wherein the means for mounting the body on a support includes a bracket attached to the end of the body opposite the recess and clamp means on the bracket for clamping a support stand to mount the body thereon, the fixing-sealing means including releasable locking means for pulling the tapered means toward the bracket into the recess of the body and holding it in the recess, the releasable locking means including an overcenter locking mechanism for securely holding the tapered means in the recess, and an adjusting bolt connected to the locking mechanism and the bracket and extending longitudinally through the body between the locking mechanism and bracket, the heat-exchanging fluid inlet and outlet passageways having openings formed in the circumferential surface of the body along opposite sides of the body for supplying the heat-exchanging fluid to the heat exchanger and removing the fluid from the heat exchanger, the openings being elongate in the direction longitudinally or axially of the body.

26. The administration set according to claim 24 wherein the means for expanding a portion of the body includes spring means for biasing the tapered means longitudinally or axially outwardly from the recess of the body to a non-sealing position wherein the heat exchanger can be placed on the body with the body received in the heat exchanger and the heat exchanger can be removed from the body, the tapered means being movable against the spring bias longitudinally or axially inwardly into the recess to a sealing position wherein the portion of the body adjacent the recess is expanded radially outwardly by the tapered means to hold and seal the heat exchanger.

27. The administration set according to claim 26 wherein the tapered means includes a frustoconical member adapted to be received in the recess of the body such that the portion of the body adjacent the recess is expanded radially outwardly by the frustoconical member.

28. The administration set according to claim 27 wherein the fixing-sealing means includes releasable locking means for pulling the frustoconical member into the recess of the body and holding it in sealing position, the releasable locking means including an overcenter locking mechanism for securely holding the frustoconical member in sealing position.

29. The administration set according to claim 26 wherein the body is formed of generally elastomeric material having a Shore A durometer of between 60 and 90.

30. The administration set according to claim 26 wherein the means for mounting the body on a support includes a bracket attached to the end of the body opposite the recess and clamp means on the bracket for clamping a support stand to mount the body thereon.

31. The administration set according to claim 30 wherein the generally cylindrical body is flared radially outwardly adjacent the bracket.

32. The administration set according to claim 30 wherein the heat-exchanging fluid inlet and outlet passageways have openings formed in the circumferential surface of the body along opposite sides of the body for supplying the heat-exchanging fluid to the heat exchanger and removing the fluid from the heat exchanger, the openings being elongate in the direction longitudinally or axially of the body.

33. The administration set according to claim 23 wherein the body is generally cylindrical, the heat exchanger including an undulated, annular barrier for separating the cardioplegia solution from the heat-exchanging fluid while permitting heat transfer through the barrier, the barrier having an inner undulated surface constituting the inner surface and defining the body-receiving passageway as generally cylindrical, and an outer undulated surface along which the solution flows.

34. The administration set according to claim 33 wherein the heat exchanger further includes a case sealingly connected to the barrier and forming a cardioplegia solution path along the barrier through the case, the case forming the bubble trap at one end of the blood/solution path for separating the trapping gas from the blood or solution, the case being adapted to be turned on the cylindrical body between a priming position wherein the bubble trap is positioned below the body and a ready position wherein the bubble trap is positioned above the body.

* * * * *